United States Patent
Murley et al.

(10) Patent No.: US 6,730,323 B1
(45) Date of Patent: May 4, 2004

(54) MICROCLYSMIC GEL FOR TREATMENT OF TISSUE TRAUMA AND BURNS

(75) Inventors: Jack C. Murley, O'Fallon, IL (US); John C. Brereton, Chesterfield, MO (US)

(73) Assignee: Care Teck Laboratories, Inc., St. Louis, MO (US)

( * ) Notice: Subject to any disclaimer, the term of this patent is extended or adjusted under 35 U.S.C. 154(b) by 757 days.

(21) Appl. No.: 08/769,596

(22) Filed: Dec. 18, 1996

(51) Int. Cl.$^7$ .............. A61K 9/14; A61K 9/00; A61K 35/34; A61K 31/715
(52) U.S. Cl. ............ 424/487; 424/486; 424/400; 424/548; 424/549; 514/55; 514/54; 514/21
(58) Field of Search ............... 514/54, 21, 55; 424/548, 549, 400, 486, 487

(56) References Cited

U.S. PATENT DOCUMENTS

| | | | |
|---|---|---|---|
| 5,036,095 A | * 7/1991 | Andermann | 514/389 |
| 5,470,911 A | * 11/1995 | Rhee et al. | 525/54.1 |
| 5,519,046 A | * 5/1996 | Noda et al. | 514/413 |
| 5,565,210 A | * 10/1996 | Rosenthal et al. | 424/426 |
| 5,670,169 A | * 9/1997 | Cornell et al. | 424/488 |

OTHER PUBLICATIONS

Hoover, J.E., "Remington's Pharmaceutical Sciences" (15$^{th}$ Ed.), Easton, PA: Mack Publishing Co. (1975), pp. 327–339 and 1452–1457.*
HCAPLUS abstract, AN 1994:245102, (1993), abstract of EP 571903 A1 to Farina et al.*

* cited by examiner

Primary Examiner—Shengjun Wang
(74) Attorney, Agent, or Firm—Paul M. Denk

(57) ABSTRACT

A therapeutic wound gel is provided which will enhance healing of the wound and reduce swelling and increase elasticity of the skin. Humatrix is bacteriostatic protectant with no bacteriocidal activity. The gel consist essentially of by weight percent, about 88–97% water, about 0.4–0.6% carbomer, about 1.2–7.8% propylene glycol, about 0.6–1.3% glycerin, about 0.5% DMDM Hydantoin, about 0–0.8% citric acid, about 0.1% chondroitin sulfate and animal protein, and about 0–0.6% triethanolamine. The gel is formed in three phases which are combined together, the first phase consisting essentially of about 88–99% of the water of the gel, the carbomer, the propylene glycol, and the glycerin; the second phase consisting essentially of the remaining water, the DMDM Hydantoin, and the citric acid if needed; and the third phase consisting essentially of the chondroitin sulfate and animal protein and the triethanolamine, if needed.

3 Claims, No Drawings

MICROCLYSMIC GEL FOR TREATMENT OF TISSUE TRAUMA AND BURNS

BACKGROUND OF APPLICATION

This invention relates to gels used to treat tissues, and in particular to a gel which stimulates wound healing in chronic wound, 1st degree, 2nd degree, and 3rd degree burns.

Major tissue trauma requires a lengthy time to heal. If the trauma is not properly treated or managed, the wound can suffer from dehydration, hyperthermia and consequent swelling, hyper-contracture, hyper-granulation, and scarring. These are all obstacles to proper healing and significantly affect health care costs.

SUMMARY OF INVENTION

One object of the present invention is to provide a gel which will enhance the healing of tissue wounds via biochemistry.

Another object is to provide such a gel which will provide rapid heat reduction for the wound bed or damaged tissue.

Another object is to provide such a gel which will reduce hyper-granulation, hyper-contracture, and scarring.

Another object is to provide such a gel which will enhance the extensibility and flexibility of human skin.

These and other objects will become apparent to those skilled in the art in light of the following disclosure and accompanying drawings.

In accordance with the invention, generally stated, a therapeutic wound gel is provided which will enhance healing of the wound and reduce swelling and improve elasticity of the skin. The gel consist essentially of by weight percentage about 88–97% water, about 0.4–0.6% carbomer, about 1.2–7.8% propylene glycol, about 0.6–1.3% glycerin, about 0.5% DMDM Hydantoin, about 0–0.8% citric acid, about 0.1% chondroitin sulfate and animal protein, and about 0–0.6% triethanolamine. The gel is formed in three phases which are combined together, the first phase consisting essentially of about 80–99% of the water of the gel, the carbomer, the propylene glycol and the glycerin; the second phase consisting essentially of the remaining water, the DMDM Hydantoin, and the citric acid if needed; and the third phase consisting essentially of chondroitin sulfate and collagen and the triethanolamine, if needed.

DESCRIPTION OF THE PREFERRED EMBODIMENT

The gel of the present invention consist of $H_2O$, carbomer, propylene glycol, glycerin, DMDM Hydantoin, citric acid, cromoist CS (a combination of chondroitin sulfate and hydrolyzed animal protein) and triethanolamine. Carbomer is a homopolymer of acrylic acid cross linked with an allyl ether of pentaery thritol or an allyl ether of sherose. available from Goodrich and which forms stable emulsions of oils in water. The propylene glycol is provided to slow down the transepidermal loss of water, and thus helps to keep the wound moist. The glycerin, when used in low concentrations, as is done herein, acts to attract moisture from the air onto the skin surface. This also aids in keeping the wound moist. DMDM Hydantoin is 1,3 dimethyl available from Lonza and is provided to long term stability and preservation. Cromoist CS is a combination of chondroitin sulfate and hydrolyzed animal protein, available from Croda, Inc. The Cromoist CS is provided to moisturize the wound and to reduce transepidermal water loss at low relative humidities. The action of the Cromoist CS increases the synergism of the propylene glycol, glycerine and DMDM Hydantoin render the gel bacteriostatic but not bacteriocidal. This product is designed to be used in conjunction with Techni-Care®, Clinical Care®, and Care-Creme® in therapeutic treatment and the extensibility and flexibility of the skin. The chondroitin sulfate in the Cromoist CS is a glycosaminoglycan which acts as a flexible connecting matrix and serves to promote and accelerate regeneration of the tissue by replicating the natural fibro-connective template and stimulating fibroblast activity. That is, it creates a precursor of collagen formation. The addition of the glycosaminglycans thus helps to increase the extensibility and flexibility of the skin while providing pain reduction by reducing the heat and swelling of the wound.

The gel is produced in a three phase process, the compositions of which are as follows:

| Component | Purpose | Amount (gm) |
|---|---|---|
| Phase A | | |
| Water | diluent | 90.70 ± 10.0 |
| Carbomer | humectant | 0.5 ± 0.2 |
| Propylene Glycol | humectant | 5.0 ± 4.0 |
| Glycerin | humectant | 1.0 ± 0.5 |
| Phase B | | |
| Water (UV sterilized) | diluent | 1.0 ± 0.5 |
| DMDM Hydantoin | | 0.5 ± 0.1 |
| Citric Acid | chelating agent | 0.70 ± 0.25 |
| Phase C | | |
| Cromoist (Chondroitin Sulfate and animal protein) | glycosaminoglycan | 0.10 ± 0.05 |
| Triethanolamine | pH adjuster | 0.50 ± 0.25 |

The gel is produced as follows: Sterile $H_2O$ and Carbomer of Phase A are initially mixed together under high shear for preferably 1–2 minutes. The propylene glycol and glycerin are added next in order, again under high shearing mixing. The components of Phase B are mixed together and then, when completely dissolved, are added to Phase A and mixed there with to produce an homogeneous mixture. The citric acid is added only if necessary to adjust the pH to a pH of between 6.5 and 7.5. The Cromoist CS, of Phase C is then added slowly to the mixture of Phase A and B. When the Cromoist has been added, the triethanolamine is added to adjust the pH of the mixture to a final pH of about 7.0. Mixing is then continued until a clear gel is obtained.

In use, once a wound has been thoroughly cleaned with an antimicrobial solution, the gel of the present invention is applied to the wound. The gel is applied in a layer that is 4 mm to 6 mm thick. The wound is then covered with a non-occlusive dressing. To maintain a moist environment, the gel is reapplied each time the dressing is changed or twice daily.

Application of the gel has been found to reduce the surface temperature of a wound by 12° C. to 18° C. in approximately three minutes. This prompt cooling reduces hyperthermia and associated tissue swelling. The temperature reduction capacity is essential to pain management attributes of this formulation and for it's use in 3rd degree bums.

As variations within the scope of the appended claims may be apparent to those skilled in the art, the foregoing description is set forth only for illustrative purposes and is not meant to be limiting.

We claim:

1. A therapeutic wound gel consisting essentially of, by weight percent, about 88–97% water, about 0.4–0.6% carbomer, about 1.2–7.8% propylene glycol, about 0.6–1.3% glycerin, about 0.5% DMDM Hydantoin, about 0–0.95% citric acid, about 0.1% chondroitin sulfate and animal protein, and about 0–0.75% triethanolamine.

2. The therapeutic would gel of claim 1 wherein the gel comprises about 0.5–0.95% citric acid and about 0.3–0.75% triethanolamine.

3. The therapeutic would gel of claim 1 wherein the gel is formed from three compositions which are combined together, the first composition consisting essentially of about 88–99% of the water of the gel, the carbomer, the propylene glycol, and the glycerin; the second composition consisting essentially of the remaining water, the DMDM Hydantoin, and 0–0.95% citric acid; and the third composition consisting essentially of the chondroitin sulfate and animal protein and triethanolamine.

* * * * *